United States Patent [19]
Hoch et al.

[11] Patent Number: 4,725,282
[45] Date of Patent: Feb. 16, 1988

[54] OXIDATIVE HAIR DYEING COMPOSITION BASED UPON A CARRIER OF LOW VISCOSITY

[75] Inventors: Dietrich Hoch, Pfungstadt; Eugen Konrad, Darmstadt, both of Fed. Rep. of Germany; Gilbert Pasquier, Marly, Switzerland; Herbert Mager, Fribourg, Fed. Rep. of Germany

[73] Assignee: Wella Aktiengesellschaft, Darmstadt, Fed. Rep. of Germany

[21] Appl. No.: 817,851

[22] PCT Filed: Apr. 15, 1985

[86] PCT No.: PCT/EP85/00165
  § 371 Date: Nov. 27, 1985
  § 102(e) Date: Nov. 27, 1985

[87] PCT Pub. No.: WO86/00223
  PCT Pub. Date: Jan. 16, 1986

[30] Foreign Application Priority Data

Jun. 27, 1984 [DE] Fed. Rep. of Germany ....... 3423589

[51] Int. Cl.$^4$ ................................................. A61K 7/13
[52] U.S. Cl. ............................................ 8/408; 8/405; 8/406; 8/407; 8/421; 8/423; 8/429; 424/70
[58] Field of Search .................... 8/405, 406, 408, 407, 8/421, 423, 429; 424/70

[56] References Cited

U.S. PATENT DOCUMENTS

| | | | |
|---|---|---|---|
| 3,530,215 | 9/1970 | Greif et al. | 424/70 |
| 3,836,537 | 9/1974 | Boerwinkle et al. | 424/71 |
| 4,009,256 | 2/1977 | Nowak, Jr. et al. | 424/70 |
| 4,031,025 | 6/1977 | Vanlerberghe et al. | 252/180 |
| 4,047,888 | 9/1977 | Papantoniou | 8/10.2 |
| 4,075,131 | 2/1978 | Sterling | 424/70 |
| 4,091,035 | 5/1978 | Clark | 260/397.25 |
| 4,150,115 | 4/1979 | Jacquet et al. | 424/70 |
| 4,153,570 | 5/1979 | Hennemann et al. | 252/121 |
| 4,273,760 | 6/1981 | Koehler et al. | 424/70 |
| 4,315,910 | 2/1982 | Nowak, Jr. et al. | 424/47 |
| 4,369,037 | 1/1983 | Matsunaga et al. | 8/405 |
| 4,507,280 | 3/1985 | Pohl et al. | 8/405 |
| 4,551,475 | 11/1985 | Eckert | 514/408 |
| 4,564,520 | 1/1986 | Ehrl et al. | 424/70 |

Primary Examiner—Prince E. Willis
Assistant Examiner—Linda D. Skaling
Attorney, Agent, or Firm—Michael J. Striker

[57] ABSTRACT

Oxidative dyeing of human hair upon the basis of a carrier and a dye mixture dissolved therein, whereby the carrier is made from (1) 16 to 30% by weight of a mixture of
 (a) 0.2–5.0% by weight of at least one physiologically harmless water soluble inorganic salt,
 (b) 1.4–5.0% by weight sodium lauryl alcohol diglycol ether sulfate,
 (c) 0.5–6.0% by weight coconut oil acid diethanol amide,
 (d) 4.0–10.0% by weight of a mixture consisting of
   60 to 80 parts by weight cetyl stearyl alcohol
   10 to 30 parts by weight glycerin-mono-di-stearate and
   0 to 20 parts by weight wool wax alcohol as well as
 (e) 0.1–2.0% by weight quaternized homopolymerisate of dimethyl amino ethyl methacrylate,
(2) 56 to 83% by weight of water,
(3) 0.1 to 5.0% by weight ammonia,
(4) 0 to 5% by weight aliphatic alcohol,
(5) 0 to 1% by weight perfume oil and
(6) 0 to 0.5% by weight of a complex former for heavy metals The oxidative hair dyeing composition has a relatively low viscosity, is quickly miscible with the hydrogen peroxide solution and can be easily distributed in the hair. It acts untangling and smoothing on the hair and can be easily and completely rinsed out of the hair after use. The composition does not show any thickening, even after a long time storage and it has the same end viscosity independent from the type and the amount of the dye or electrolyte addition.

10 Claims, No Drawings

OXIDATIVE HAIR DYEING COMPOSITION BASED UPON A CARRIER OF LOW VISCOSITY

Oxidative hair dyeing compositions in form of cremes have presently reached a particular importance. Such hair dyeing compositions generally contain as the most important oxidative dyes p-substituted benzene derivatives like, for example, 1,4-diaminobenzene, 2,5-diaminotoluene, p-aminophenol and 2,5-diaminibenzyl alcohol. They are called developing substances. The developing substances must be used in combination with suitable coupler substances. In particular, certain m-substituted benzol derivatives or certain pyridine derivatives are used as coupler substances. Examples for customary coupler substances are resocino 1,4-chlororesorcinol, 4-hydroxy-1,2-methylene dioxybenzene, 4-amino-1,2-methylene dioxy benzene, 2-methyl resorcinol, 2,4-dihydroxy phenol ether, 4-hydroxy indole, 1-naphthol, m-aminophenole, m-phenylene diamine and m-phenylene diamine derivatives.

Customary oxidative hair dyeing compositions are alkaline adjusted, preferably by adding ammonia or monoethanol amine.

The developing substances and coupler substances are very often present in form of their chlorides or sulfates, whereby the corresponding ammonium salts are formed after adding ammonia. These salts act against the forming of emulsion and reduce their stability in creme like oxidative hair dyeing compositions together with the developers, the couplers and, if need be, the direct dyeing dye substances contained therein. In particular in dark dye rich hair dyeing compositions there is always the danger of an emulsion separation.

Hitherto, it had been required to adjust the consistency of customary creme like oxidative hair dyeing compositions to a high viscosity (above of about 10,000 mPa.$_s$, Stab II/30° C./20 g). Thus separating phenomenons were avoided and the possibility existed to charge the emulsion with high constituents of dyes and electrolytes.

Above all fatty alcohols and fatty amides are used in the aforedescribed customary hair dyeing compositions for increasing the viscosity. In order to obtain a good emulsion stability these thickeners must be used in high concentrations of about 15 to 30% by weight. Oxethylized fatty alcohols, fatty alcohol sulfates and oxethylized fatty alcohol sulfates are used as emulsifiers in customary creme like hair dyeing compositions.

If the viscosity of the hair dyeing compositions are high, these compositions are hard to distribute in hair. Therefore, they usually have to be applied with a brush. Therefore, the application onto the hair with the assistance of an emulsion test flask and thereby an application by the customer himself is not possible. Due to the high viscosity, which still increases due to the partial evaporation of liquid during the dyeing treatment, the complete rinsing after the hair dyeing treatment is made more difficult so that a subsequent hair washing is indispensable.

Before the start of the hair dyeing the creme like oxidative hair dyeing composition is admixed with an aqueous hydrogen peroxide solution, for example, a 6% $H_2O_2$-solution, customarily at a ratio of 1:1.

The hydrogen peroxide solution may be present as a clear or a turbid solution, whereby a latex dispersion is used as a turbidity substance, for example.

A further disadvantage of customarily highly viscous hair dyeing compositions consists in that its viscosity increases during storage, so that the removal from the tube is made more difficult and that the admixing with the hydrogen peroxide solution requires more time.

It is therefore an object of the subject application to provide an oxidative hair dyeing composition which has a lower viscosity than the aforedescribed known compositions, which does not run off the hair and which in furtherance does not have the described disadvantages of known creme like hair dyeing compositions.

In contrast thereto, it now had been found that novel low viscous oxidative hair dyeing compositions can be made with considerably improved characteristics, wherein the addition of dyes and electrolytes does not act destabilizing on the emulsion, but in contrast thereto acts in a stabilizing manner with respect to preventing of a phase separation as well as maintaining the adjusted viscosity during storage.

Therefore, the subject matter of the subject invention are therefore compositions for an oxidative dyeing of human hair upon the basis of a carrier and a dye mixture dissolved therein, characterized in that the carrier is made from (1) 16 to 30% by weight of a mixture of
   (a) 0.2–5.0% by weight of at least one physiologically harmless water soluble inorganic salt,
   (b) 1.4–5.0% by weight sodium lauryl alcohol diglycol ether sulfate,
   (c) 0.5–6.0% by weight coconut oil acid diethanol amide,
   (d) 4.0–14.0% by weight of a mixture consisting of
      60 to 80 parts by weight cetyl staryl alcohol
      10 to 30 parts by weight glycerin-mono-distarate and
      0 to 20 parts by weight wool wax alcohol as well as
   (e) 0.1–2% by weight quaternized homopolymerisate of dimethyl amino ethyl methacrylate,
(2) 56 to 83% by weight water
(3) 0.1 to 5.0% by weight ammonia,
(4) 0 to 5% by weight aliphatic alcohol,
(5) 0 to 1% by weight perfume oil and
(6) 0 to 0.5% by weight of a complex former for heavy metals.

The aforementioned percentage data relate always to the total amount of the oxidative hair dyeing composition.

In the inorganic salt the preferred amounts are 1.0 to 3.0% by weight, particularly preferred is 2.5% by weight. The sodium lauryl alcohol diglycol ether sulfate is contained preferably in an amount of 2.0 to 3.5% by weight and particularly preferred in an amount of 2.8% by weight. The coconut oil acid diethanol amide is contained preferably in an amount of 2.0 to 4.0% by weight, in particular 3.0% by weight. The component (d), which in furtherance is called a wax mixture, is contained preferably in an amount of 10.0 to 14.0% by weight and particularly preferred in an amount of 12% by weight. The water content of the carrier is at 56 to 83% by weight and is preferably about 60 to 70% by weight. The quaternized homopolymerisate of dimethyl aminoethyl methacylate, which is quaternized preferably at 75, for example, with dimethyl sulfate, should be contained in particular in an amount of 0.1 to 0.5% by weight and particularly preferred in an amount of 0.25% by weight.

The carrier of the composition in accordance with the invention is adjusted to a pH-value of about 8.0 to 11.5 by a content of about 0.1 to 5.0% by weight ammonia.

In particular ammonium-, sodium- or potassium sulfite, sulfate-or-chloride are considered as pysiologically harmless water soluble inorganic salts, whereby the total amount of of these salts contained in the composition is preferably 1.0 to 3.0% by weight.

For example, the sodium lauryl alcohol diglycol ether sulfate may be present in form of a commercially available 28% aqueous solution. Examples of suitable cetyl stearyl alcohols are the commercial products Lanette W ® and Lanette O of Firma Henkel, Düsseldorf. For example, as a suitable glycerin-mono-di-stearate one can use one with a 30° to 35° by weight monoester content (for example, commercial product Tegin ® of Firma Goldschmidt, Essen, Germany). As an example for a commercially available quaternized homopolymerisate of dimethyl aminoethyl methacrylate we would like to mention the commercial product PLEX 7525 of Firma Röhm, Darmstadt.

If need be, the oxidative hair dyeing compositions may contain as aliphatic alcohol, for example, ethanol or isopropanol in an amount of up to 5% by weight as well as complex formers for heavy metals, for example, ethylene diamine tetraacetate and nitrilo-triacetic acid in an amount of up to 0.5% by weight. Perfume oils may be contained in the compositions in an amount of about 1% by weight.

The dye mixture contained in the oxidative hair dyeing compositions consists of at least one coupler substance and at least one developing substance and, if need be in addition with selfcoupling dye presteps and dyes which can be directly applied on the hair.

The developing and coupler substances are used in the hair dyeing agents as such or in form of their physiologically harmless salts with inorganic or organic acids as, for example, as a chloride, sulfate, phosphate, acetate, propionate, lactate or citrate.

The coupler substances are generally used in about equimolar amounts with respect to the employed developing substances. Even if the equimolar use is advantageous, it is not disadvantageous if the coupler substances are used with a certain excess or in a lesser amount. Furthermore, it is not required that the developing components and the coupler components represent uniform products, on the contrary, the developing component may represent a mixture of known developing substances as well as the coupler component may be a mixture of known coupler substances.

The hair dyeing composition contain as known coupler substances, in particular, 2-naphthol, 4-methoxy-1-naphthol, resorcinol, 4-chlororesorcinol, 4,6-dichlororesorcinol,2-methyl resorcinol, m-aminophenol,4-hydroxy-1,2-methylene dioxybenzene, 4-amino-1,2-methylene dioxybenzene,4-($\beta$-hydroxyethylamino)-1,2-methylene dioxy benzene and 5-amino-2-methylphenol. Further suitable coupler substances are, for example, 2,4-dihydroxy phenol ether like 2,4-dihydroxy anisol and 2,4-dihydroxy phenoxy ethanol.

Of the known developing substances above all 1,4-diaminobenzene, 2,5-diaminotoluene, 2,5-diaminoanisol,2,5-aminobenzyl alcohol, 3-methyl-4-aminophenol, 2-($\beta$-hydroxyethyl)-1,4-diaminobenzene, tetraaminopyrimidine and 4-aminophenol are considered as a constituent of the hair dyeing compositions in accordance with the invention.

The total amount of the developing substance-coupler substance combination contained in the described hair dyeing compositions should be about 0.1 to 5.0% by weight, in particular 0.5 to 5.0% by weight.

For obtaining certain color shades there may also be contained customary directly applied dyes, for example, tripenyl menthane dyes like Diamond Fuchsin (C.I.42 510) and Leather Ruby HF (C.I. 42 520), aromatic nitro dyes like 2-amino-4,6-dinitro-phenol, 2-nitro-4-($\beta$-hydroxyethylamino)anilin,2-N-$\beta$,$\gamma$-dihydroxy-propylamino-5-(N-methyl,N-hydroxyethyl) amino-nitrobenzene and 2-amino-4-nitrophenol, azo dyes like Acid Brown 4 (C.I. 14 805) and Acid Blue 135 (C.I. 13 385)anthraquinone dyes like Disperse Violet 4 (C.I.61 105), Disperse Blue 1 (C.I. 64 500), Disperse Red 15 (C.I. 60 710), Disperse Violet 1 (C.I. 61 100), moreover 1,4,5,8-tetra amino anthraquinone and 1,4-diamino anthraquinone.

The hair dyeing composition may in furtherance contain selfcoupling dye presteps like, for example, 2-amino-5-methyl phenol, 2-amino-6-methyl phenol, 2-amino-5-ethoxyphenol or also 2-propyl amino-5-aminopyridine.

The total amount of the dye mixture in the compositions described here are about 0.1 to 5.0% by weight, preferably 0.5. to 5.0% by weight.

The oxidative hair dyeing composition in accordance with the invention represents a mixture from the carrier and the dye mixture.

During use one mixes the hair dyeing composition immediately before use at about a weight ratio of 5:1 to 1:4 with an oxidative composition and applies an amount of this mixture sufficient for the hair dyeing treatment, generally about 60 to 200 g, depending on the fullness of hair. Mainly hydrogen peroxide is considered as the oxidative substance for developing the hair dyeing, for example, as a 6% aqueous solution or their addition compounds of urea, melamine or sodium borate. One lets the mixture react on the hair at 15° to 50° for about 10 to 45 minutes, preferably for 30 minutes and therafter rinsing the hair with water and drying. If need be, an afterrinsing is performed subsequent to this rinsing with a weak physiologically harmless organic acid like, for example, citric acid or wine acid.

The hair dyeing composition in accordance with the invention is very easiiy and quickly miscible with the hydrogen peroxide solution due to the relatively low viscosity of the hair dyeing composition which is about 400 to 4000, preferably 1000, mPa.s at 30° C. (measured with the viscous scale of Haake with Stab II and a superimposed layer weight of 20 gram), whereby the hair dyeing composition does not have to be homogenized, as well as due to the high wetting agent content (sodium lauryl alcohol diglycol ether sulfate). It is applied to the hair to be dyed, after mixing, either with a brush or preferably with the application bottle.

When dyeing the regrown hair only the base of the hair is treated with the mixture consisting of the hair dyeing composition and the hydrogen peroxide solution. The dye mixture is then applied to the length of the hair and the tips of the hair by combing, after a reaction time of about 5 to 40 minutes at 15° to 50° C. The hair is very well distributable in the hair. Therefore, the corresponding low mechanical stress on the hair during combing is advantageous in particular with porous hair. Moreover, the hair dyeing composition described acts in a detangling and smoothing manner on the hair, whereby a distribution of the composition in the hair is also facilitated.

After reacting of the hair dyeing composition it can be easily rinsed out off the hair again, so that a washing of the hair is no longer required.

When using the aforedescribed hair dyeing composition the generally porous hair is simultaneously untangled and receives a comfortable smooth touch, so that it can be very well combed without any additional use of a caring agent or a hair rinsing.

A thickening after a long time of storage cannot be noticed with the hair dyeing composition in accordance with the invention. In furtherance the compositions have the surprising characteristic that they result in the same end viscosity independent from the type and quantity of the dye or electrolyte addition contained therein. Thereby, it is possible to use the same carrier for all color shades of a hair dyeing series. This considerably facilitates the making of a hair dyeing series. In creme like oxidative hair dyeing compositions in accordance with the state of the art the carrier must be different for the given color shades. For example, in dark shades of commercially available creme hair dyes the content of thickener agents is higher than in lighter dye shades.

The following examples will explain the subject matter of the subject invention in more detail

EXAMPLES

| Example 1 | Example 2 | (black shades) |
|---|---|---|
| (carrier) | | |
| 0.50 g | 0.50 g | sodium sulfite, free of water |
| 1.00 g | 2.00 g | sodium sulfate, free of water |
| 11.00 g | 10.00 g | sodium lauryl alcohol diglycol ether sulfate (28% aqueous solution) |
| 2.00 g | 3.00 g | coconut oil acid diethanol amide. |
| 14.00 g | 12.00 g | of a mixture of 70 parts by weight of cetyl stearyl alcohol, 22 parts by weight of glycerin-mono-distearate and 8 parts by weight wool wax alcohol. |
| 0.35 g | 0.25 8 | polydimethyl amino ethyl methacrylate, 70% quaternized |
| 2.50 g | 2.50 g | ammonia |
| 63.75 g | 64.85 g | water |
| 95.10 g | 95.10 g | |
| (Dye mixture) | | |
| 0.20 g | 0.20 g | m-aminophenyl |
| 0.50 g | 0.50 g | 2,4-diaminophenetolsulfate |
| 3.00 g | 3.00 g | 2,5 diaminotoluenesulfate |
| 1.20 g | 1.20 g | resorcinol |
| 4.90 g | 4.90 g | |
| 100.00 g | 100.00 g | |

40 g of the creme like hair dyeing composition in accordance with example 1 or 2 are admixed with 40 g of a customary 6% aqueous hydrogen peroxide solution. The complete admixture is performed in a few seconds.

The mixture is applied to the gray hair aftergrowth of black dyed gray hair which 6 weeks before had been dyed. After a reaction time of 20 minutes at 45° C. the hair dyeing mixture is distributed to the length and the tips of the hair by means of combing. Due to the easy distributibilty of the composition in accordance with the invention this is performed quicly and with the greatest possible hair protection. The mixture remains for reaction for a few further minutes at room temperature. Finally, the hair dyeing mixture is rinsed out of the hair with warm water, whereby the hair is not after-shampooned.

The hair which had been treated in this manner is uniformly dyed black from the base to the tips of the hair. The hair is very well combable in the wet condition as well as in the dry condition and is well fixable. Moreover, it has a comfortable touch. No residues of the dye mixture are noticeable in the hair.

The hair dyeing composition in accordance with example 1 and 2 do not change their viscosity in the temperature range of 5° to 40° C., even after a long storage time. A phase separation can also not be seen.

| Example 3 | Example 4 | (light blond shades) |
|---|---|---|
| (carrier) | | |
| 1.00 g | 0.50 g | sodium sulfite, free of water |
| 1.00 g | — | sodium chloride |
| — | 2.00 g | sodium sulfate, free of water |
| 10.00 g | 10.00 g | sodium lauryl alcohol diglycol ether sulfate (28% aqueous solution) |
| 3.50 g | 3.00 g | coconut oil acid diethanol amide |
| 10.00 g | 12.00 g | of a mixture of 70 parts by weight of cetyl stearyl alcohol, 22 parts by weight of glycerin-mono-distearate and 8 parts by weight wool wax alcohol |
| 1.00 g | 1.00 g | polydimethyl aminoethyl methacrylate, 70% quaternized, 25% aqueous solution |
| 10.00 g | 10.00 g | ammonia, 25% aqueous solution |
| 63.00 g | 61.00 g | water |
| 99.50 g | 99.50 g | |
| (Dye mixture) | | |
| 0.35 g | 0.35 g | 2,5-diaminotoluene sulfate |
| 0.15 g | 0.15 g | resorcinol |
| 0.50 g | 0.50 g | |
| 100.00 g | 100.00 g | |

The application of the creme like hair dyeing composition in accordance with examples 3 and 4 is performed in the same manner as described for examples 1 and 2, however on a gray hair aftergrowths which had been dyed blond on a human hair 6 weeks before.

After the dyeing treatment the hair is uniformly dyed blond and has all the advantageous characteristic as stated heretofore with respect to the examples 1 and 2. The compositions in accordance with example 3 and 4 do not change their viscosity during a long storage time and also do not have a phase separation.

We claim:

1. Composition for oxidative dyeing of human hair having a viscosity of 400–4000 mPa.s upon the basis of a carrier and a dye mixture dissolved therein, said carrier comprising
   (1) 16 to 30% by weight of a mixture of
      (a) 0.2–5.0% by weight of at least one physiologically harmless water soluble inorganic salt,
      (b) 1.4–5.0% by weight sodium lauryl alcohol diglycol ether sulfate,
      (c) 0.5–6.0% by weight coconut oil acid diethanol amide,
      (d) 4.0–14.0% by weight of a mixture consisting of
         60 to 80 parts by weight cetyl stearyl alcohol,
         10 to 30 parts by weight glycerin-mono-di-stearate and
         0 to 20 parts by weight wool wax alcohol, as well as
      (e) 0.1–2.0% by weight homopolymerisate of dimethyl amino ethyl methacrylate, 60–80% quaternized with $C_1$–$C_4$-alkylhalide or $C_1$–$C_4$-alkylsulfate,
   (2) 56 to 83% by weight water,
   (3) 0.1 to 5.0% by weight ammonia,
   (4) 0 to 5% by weight aliphatic alcohol, (5) 0 to 1% by weight perfume oil and (6) 0 to 0.5% by weight of a complex former for heavy metals.

2. Composition for oxidative dyeing of human hair having a viscosity of 400–4000 mPa.s upon the basis of a carrier and a dye mixture dissolved therein, said carrier comprising (1) 16 to 30% by weight of a mixture of
  (a) 1.0–3.0% by weight of a physiologically harmless water soluble inorganic salt,
  (b) 2.0–3.5% by weight sodium lauryl alcohol diglycol ether sulfate,
  (c) 2.0–4.0% by weight coconut oil acid diethanol amide,
  (d) 10.0–14.0% by weight of a mixture, consisting of
    60 to 80 parts by weight cetyl stearyl alcohol,
    10 to 30 parts by weight glycerin-mono-di-stearate and
    0 to 20 parts by weight wool wax alcohol, as well as
  (e) 0.1–0.5% by weight homopolymerisate of dimethyl aminoethyl methacrylate, 60–80% quaternized with $C_1$–$C_4$-alkylhalide or $C_1$–$C_4$-alkylsulfate,
(2) 56 to 83% by weight water,
(3) 0.1 to 5.0% by weight ammonia,
(4) 0 to 5% by weight aliphatic alcohol,
(5) 0 to 1% by weight perfume oil and
(6) 0 to 0.5% by weight of a complex former for heavy metals.

3. Composition in accordance with claim 1, consisting of
0.5–5.0% by weight of a dye mixture,
2.5% by weight of a physiologically harmless water soluble inorganic salt,
2.8% by weight sodium lauryl alcohol diglycol ether sulfate,
3.0% by weight coconut oil acid diethanol amide,
8.4% by weight cetyl stearyl alcohol,
2.6% by weight glycerin-mono-di-stearate,
1.0% by weight wool wax alcohol,
0.25% by weight homopolymerisate of dimethyl aminoethyl methacrylate, 60–80% quaternized with $C_1$–$C_4$-alkylhalide or $C_1$–$C_4$-alkylsulfate,
2.5% ammonia and
72.95–76.45% by weight water.

4. Composition in accordance with claim 1, characterized in that the physiologically harmless water soluble salt is selected from ammonium-, sodium-or potassium-sulfite, -sulfate or-chloride.

5. Composition in accordance with claim 1, characterized in that the dye mixture contains at least one of the developing substances 1,4-diaminobenzene, 2,5-diaminotoluene,2,5-diaminobenzyl alcohol, 4-aminophenol, 3-methyl-4aminophenol, 2,5-diaminoanisol and tetraamino pyrimidine.

6. Composition in accordance with claim 1, characterized in that the dye mixture contains at least one of the coupler substances 1-naphthol, 4-methyoxy-1-naphthol, resorcinol, 4-chlororesorcinol, 4,6-dichlororesorcinol, 2-methyl resorcinol, 2,4-dihydroxy-anisol, 2,4-dihydroxy phenoxy ethanol, 4-hydroxy-1,2-methylene dioxy benzene, 4-(β-hydroxyethylamino)-1,2-methylene dioxy benzene, m-aminophenol and 5-amino-2-methylphenol.

7. Composition in accordance with claim 1, characterized in that the total amount of the developing substance-coupler substance-combination contained in the dye mixture is from 0.5 to 5.0% by weight.

8. Composition in accordance with claim 1, characterized in that the dye mixture contains as a dye component 2-amino-5-methylphenol, 2-amino-6-methylphenol, 2-amino-5-ethoxyphenol or 2-propyl amino-5-aminopyridine.

9. Composition in accordance with claim 1, characterized in that the dye mixture contains at least one of the directly coloring dyes Diamond Fuchsin (C.I. 42 510), Leather Ruby HF (C.I. 42 520), 2-amino-4,6-dinitrophenol, 2-nitro-4-(β-hydroxyethylamino)-anilin, 2-N-β,γ-dihydroxy propyl amino-5-(N-methyl, N-hydroxyethyl) aminonitrobenzene, 2-amino-4-nitrophenol, Acid Brown 4 (C.I. 14 805), Acid Blue 135 (C.I. 13 385), Disperse Red 15 (C.I. 60 710), Disperse Violet I (C.I. 61 100), 1,4,5,8-tetra-amino-anthraquinone and 1,4-diamino-anthraquinone.

10. Composition in accordance with claim 2, consisting of 0.5–5.0% by weight of a dye mixture,
2.5% by weight of a physiologically harmless water soluble inorganic salt,
2.8% by weight sodium lauryl alcohol diglycol ether sulfate,
3.0% by weight coconut oil acid diethanol amide
8.4% by weight cetyl stearyl alcohol
2.6% by weight glycerin-mono-di-stearate
1.0% by weight wool wax alcohol
0.25% by weight quaternized homopolymerisate of dimethyl aminoethyl methacrylate,
2.5% ammonia
72.95–76.45% by weight water.

* * * * *